(12) United States Patent
Wenstrom, Jr. et al.

(10) Patent No.: US 6,325,804 B1
(45) Date of Patent: Dec. 4, 2001

(54) METHOD FOR FIXING A GRAFT IN A BONE TUNNEL

(75) Inventors: Richard F. Wenstrom, Jr., Norwood; Izi Bruker, Wayland; Steven M. Bowman, Sherborn; Gregory Whittaker, Stoneham, all of MA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/604,867

(22) Filed: Jun. 28, 2000

(51) Int. Cl.$^7$ ................................... A61B 17/56
(52) U.S. Cl. ............................... 606/72; 606/88
(58) Field of Search ............... 606/72, 88, 151, 606/232

(56) References Cited

U.S. PATENT DOCUMENTS

| | | |
|---|---|---|
| 4,898,156 | 2/1990 | Gatturna et al. . |
| 4,899,743 | 2/1990 | Nicholson et al. . |
| 4,950,270 | 8/1990 | Bowman et al. . |
| 4,968,315 | 11/1990 | Gatturna . |
| 5,147,362 | 9/1992 | Goble . |
| 5,356,413 | 10/1994 | Martins et al. . |
| 5,372,599 | 12/1994 | Martins . |
| 5,374,269 * | 12/1994 | Rosenberg ............................. 606/80 |
| 5,393,302 * | 2/1995 | Clark et al. ........................... 623/13 |
| 5,431,651 | 7/1995 | Goble . |
| 5,562,669 * | 10/1996 | McGuire ................................ 606/72 |
| 5,643,266 * | 7/1997 | Li .......................................... 606/72 |
| 5,702,422 * | 12/1997 | Stone ................................... 606/232 |
| 5,766,250 * | 6/1998 | Chervitz et al. ....................... 623/13 |
| 5,871,504 * | 2/1999 | Eaton et al. ......................... 606/232 |
| 5,941,883 * | 8/1999 | Sklar ..................................... 606/88 |
| 5,989,253 * | 11/1999 | Bigliardi .............................. 606/72 |
| 6,113,604 * | 9/2000 | Whittaker et al. .................... 606/72 |
| 6,132,433 * | 10/2000 | Whelan ................................ 606/72 |
| 6,152,928 * | 11/2000 | Wenstrom, Jr. ...................... 606/72 |
| 6,214,007 * | 4/2001 | Anderson ............................. 606/73 |
| 6,245,073 * | 6/2001 | Conteduca et al. .................. 606/72 |
| 6,254,604 * | 7/2001 | Howell ................................. 606/96 |

* cited by examiner

Primary Examiner—Paul J. Hirsch
Assistant Examiner—Michael B. Priddy
(74) Attorney, Agent, or Firm—Emil Richard Skula

(57) ABSTRACT

A method for performing an anterior cruciate ligament repair procedure wherein a bone plug attached to a section of tendon or ligament is fixed in a bone tunnel. The method utilizes an adhesive to secure the bone block in the bone tunnel.

21 Claims, 15 Drawing Sheets

METHOD FOR FIXING A GRAFT IN A BONE TUNNEL

FIELD OF THE INVENTION

The field of art to which this invention relates is orthopedic surgical methods, in particular, surgical procedures for fixating bone grafts in bone tunnels.

BACKGROUND OF THE INVENTION

Joint injuries may commonly result in the complete or partial detachment of ligaments, tendons and soft tissues from bone. Tissue detachment may occur in may ways, e.g., as the result of an accident such as a fall, overexertion during a work-related activity, during the course of an athletic event, or in any one of many other situations and/or activities. These types of injuries are generally the result of excess stress or extraordinary forces being placed upon the tissues.

In the case of a partial detachment, commonly referred to under the general term "sprain", the injury frequently heals without medical intervention, the patent rests, and care is taken not to expose the injury to undue strenuous activities during the healing process. If, however, the ligament or tendon is completely detached from its attachment site on an associated bone or bones, or if it is severed as the result of a traumatic injury, surgical intervention may be necessary to restore full function to the injured joint. A number of conventional surgical procedures exist for re-attaching such tendons and ligaments to bone.

One such procedure involves the re-attachment of the detached tissue using "traditional" attachment devices such as staples, sutures, and bone screws. Such traditional attachment devices have also been used to attach tendon or ligament grafts (often formed from autogenous tissue harvested from elsewhere in the body) to the desired bone or bones.

In U.S. Pat. No. 4,950,270, a surgical procedure is disclosed to replace a damaged anterior cruciate ligament ("ACL") in a human knee. Initially bone tunnels are formed through the tibia and femur at the points of normal attachment of the anterior cruciate ligament. Next, a ligament graft with a bone block on one of its ends is sized so as to fit within the bone tunnels. Suture is then attached to the bone block and thereafter passed through the tibia and femoral bone tunnels. The bone block is then pulled through the tibia tunnel and up into the femoral tunnel using the suture. As this is done, the graft ligament extends back out of the femoral tunnel, across the interior of the knee joint, and then through the tibial tunnel. The free end of the graft ligament resides outside the tibia, at the anterior side of the tibia. Next, a bone screw is inserted between the bone block and the wall of femoral bone tunnel so as to securely lock the bone block in position by a tight interference fit. Finally, the free end of the graft ligament is securely attached to the tibia.

In U.S. Pat. No. 5,147,362, another ACL reconstruction procedure is disclosed. Aligned femoral and tibia tunnels are initially formed in a human knee. A bone block with a graft ligament attached thereto is passed through the tunnels to a blind end of the femoral tunnel where the block is fixed in place by an anchor. The ligament extends out of the tibia tunnel, and the end is attached to the tibia cortex by staples or the like. Alternatively, the end of the ligament may be fixed in the tibia tunnel by an anchor or by an interference screw.

Various types of ligament and/or suture anchors for attaching soft tissue to bone are also well known in the art. A number of these devices are described in detail in U.S. Pat. Nos. 4,898,156; 4,899,743; 4,968,315; 5,356,413; and 5,372,599, which are incorporated by reference in their entirety.

One known method for anchoring bone blocks in bone tunnels is through "cross-pinning" technique, in which a pin, screw or rod is driven into the bone transversely to the bone tunnel so as to intersect the bone block and thereby cross-pin the bone block in the bone tunnel. In order to provide for proper cross-pinning of the bone block in the bone tunnel, a drill guide is generally used. The drill guide serves to ensure that the transverse passage is positioned in the bone so that it will intersect the appropriate tunnel section and the bone block.

U.S. Pat. No. 5,431,651, discloses a cross-pin screw made from a broad absorbable material which is absorbed by the body over time, thereby eliminating any need for the cross-pin screw to be removed in a subsequent surgical procedure.

Although the soft tissue attachment procedures of the prior art have proven to be beneficial, there is a continuing need in this art for novel, improved surgical procedures, particularly in the area of anterior cruciate ligament reconstruction.

SUMMARY OF THE INVENTION

Accordingly it is an object of the present invention, to provide a method for fixing a bone block in a bone tunnel such that the bone block is retained in the tunnel by a bone cement or bone glue, thereby eliminating the need for a cross-pin or screw or other mechanical fastening device to secure the bone block.

It is a further object of the present invention to provide a novel method of graft fixation in an anterior cruciate ligament reconstruction procedure using a bone cement or bone glue.

Therefore, a novel method of performing a surgical reconstruction of an anterior cruciate ligament is disclosed. The method consists of providing a bone-tendon graft comprising at least one bone plug connected to a section of tendon. The bone plug has an outer surface. Next, a substantially longitudinal bone tunnel is drilled into a patient's tibia, and a substantially longitudinal bone tunnel is drilled into the patient's femur. The femoral bone tunnel and the tibial bone tunnel are drilled so as to be in substantial alignment. Each bone tunnel has an inner surface. The bone plug is then inserted into the femoral tunnel such that the tendon extends from the femoral plug, out of the femoral bone tunnel, and into the tibial bone tunnel. And, a bone glue or cement is introduced into the femoral tunnel such that the glue or cement is in at least partial contact with the outer surface of the bone plug and the inner surface of the femoral bone tunnel, thereby securing the bone plug in the femoral tunnel.

Yet another aspect of the present invention is the above-described method wherein the bone glue or cement is inserted into the femoral bone tunnel prior to inserting the bone plug.

Still yet another aspect of the present invention is a method of securing a bone plug in a bone tunnel. A bone tunnel is drilled into a bone. A bone plug is provided. A glue or cement is introduced into the bone tunnel to secure the bone plug in the bone tunnel.

These and other advantages of the present invention will become more apparent from the following description and accompanying drawings.

DESCRIPTION OF THE PREFERRED EMBODIMENTS

Figure 1:
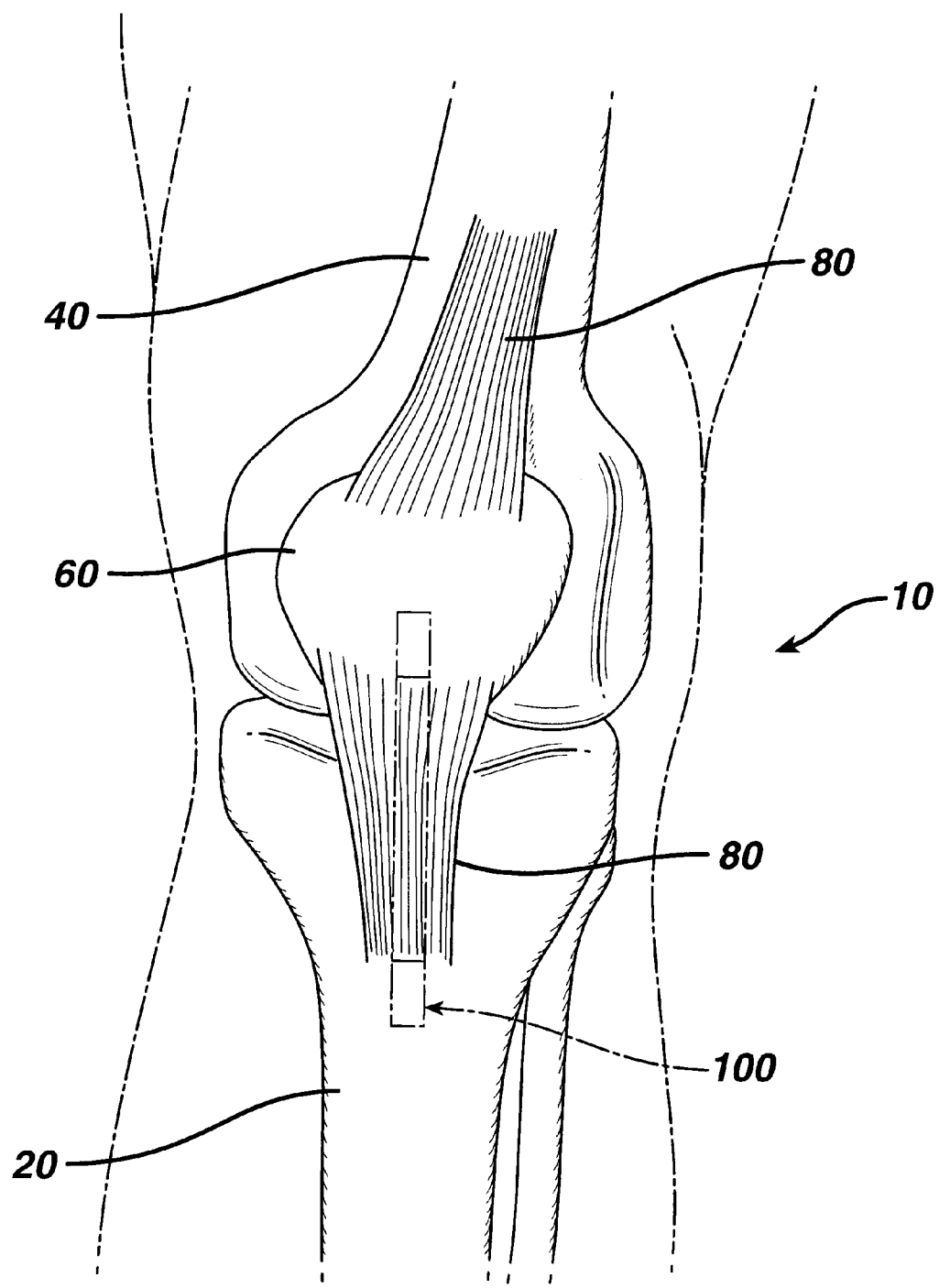
FIG. 1 illustrates a human knee prior to harvesting a bone-tendon-bone graft; the outline of the graft on the patella, patellar tendon, and tibia is shown by phantom lines.
Figure 2:
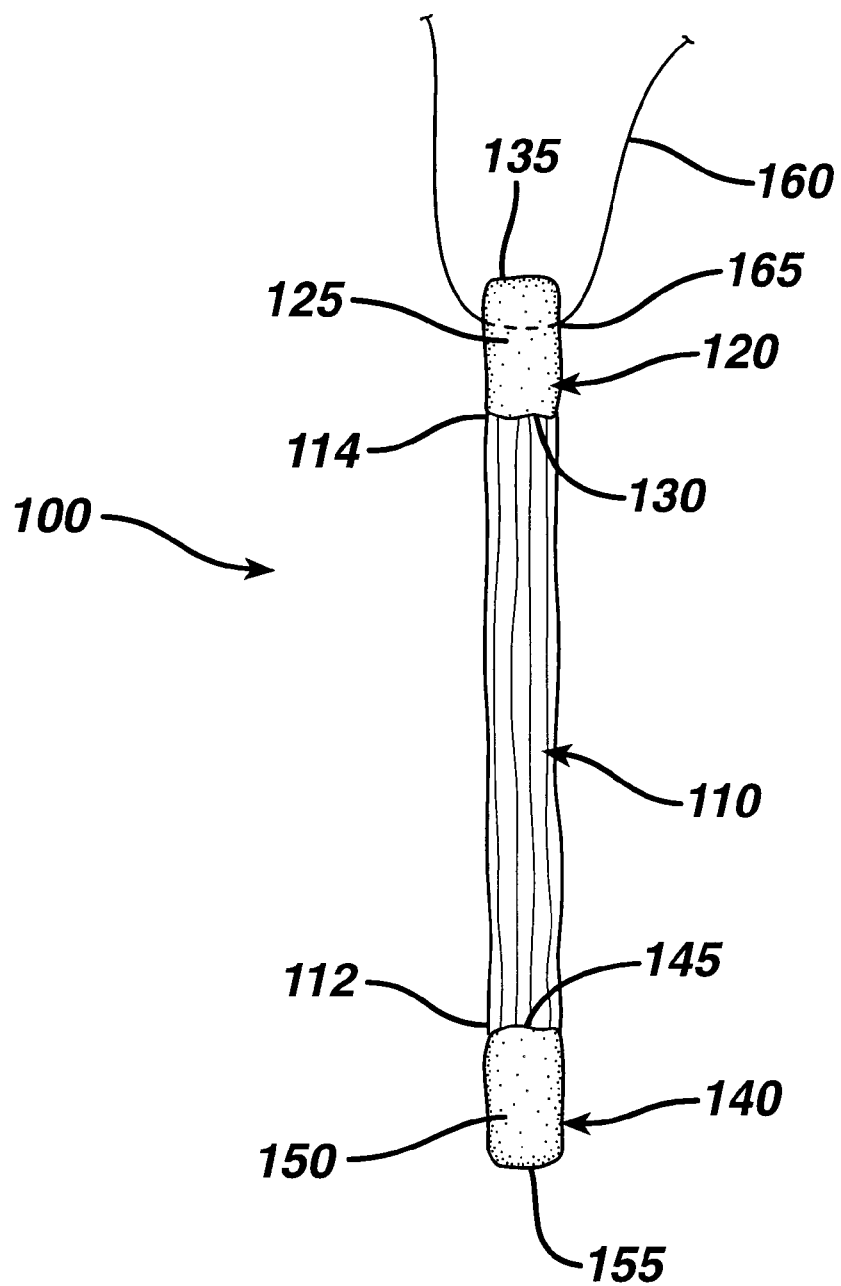
FIG. 2 illustrates a bone-tendon-bone graft after harvesting; the bone plug that is inserted into the femur has a suture mounted thereto.

The terms "bone cement" and "bone glue" are used interchangeably herein when describing the surgical procedures of the present invention. The term "tendon" as used herein is defined to include both tendons and ligaments. The bone-tendon-bone ACL reconstruction surgical procedures of the present invention are initiated by first providing a bone-tendon-bone graft. Also, depending upon the particular circumstances surrounding an individual patient and the particular injury, a bone-tendon graft could also be used having a single bone plug. As seen in FIG. 1, knee joint 10 consisting of a tibia 20, femur 40, and a patella 60 having patella tendon 80 is illustrated. An autologous bone-tendon-bone graft 100 useful in the procedure of the present invention is illustrated in FIGS. 1 and 2. The graft 100 is harvested in a conventional manner. The graft 100 is seen to have tendon section 110 having proximal end 112 and distal end 114. The femoral bone plug 120 is seen to be cut out from the patella 60. The bone plug 120 is seen to have outer surface 125, proximal end 130 connected to the distal end 114 of tendon section 110 and distal end 135. The tibia bone plug 140 is seen to be cut from tibia 20, and is seen to have distal end 145 connected to the proximal end 112 of tendon 110. The bone plug 140 is also seen to have outer surface 150 and distal end 155. Suture 160 is seen to be inserted through tunnel 165.

Figure 3A:
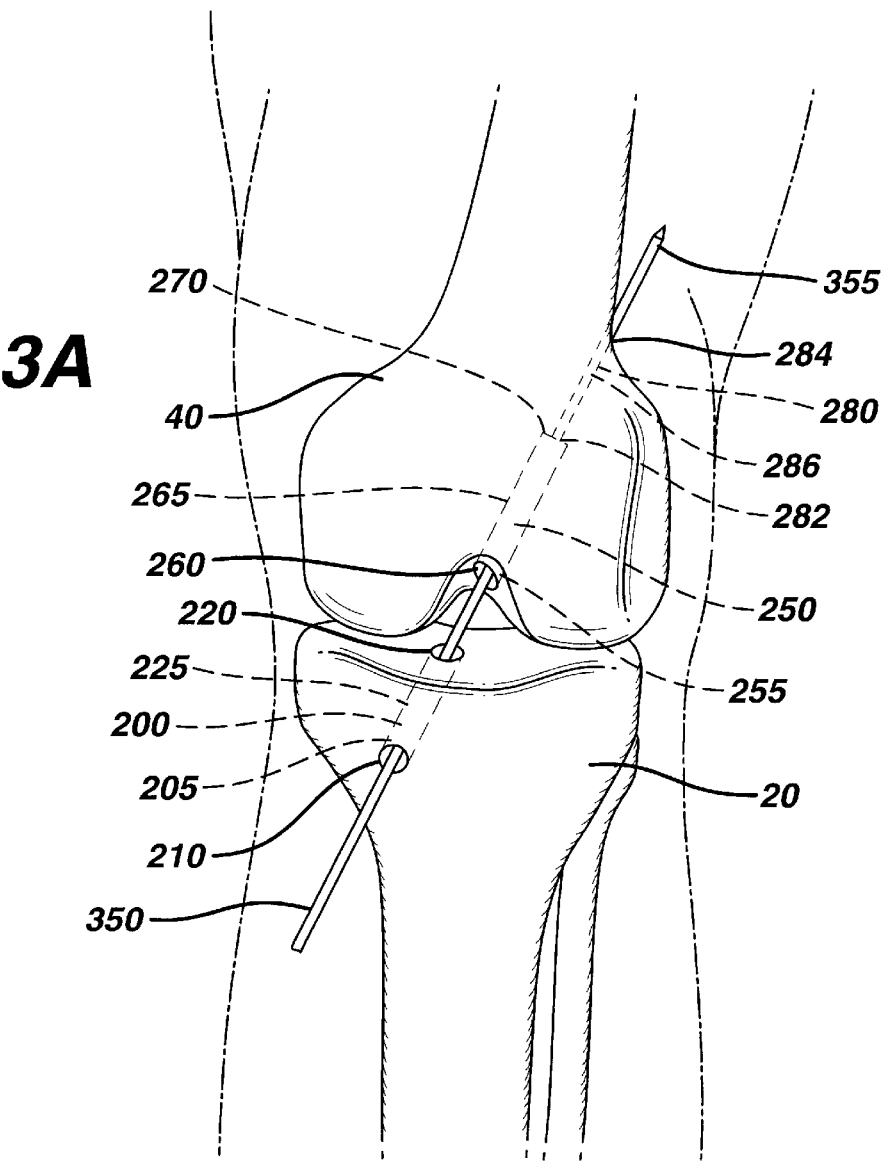
FIG. 3A illustrates a knee after a pilot drill was used to drill a series of pilot holes into the tibia and femur of a knee joint, including the suture tunnel, and after a conventional concentric bone drill was placed over the pilot drill to drill out the tibial and femoral bone tunnels; the pilot drill is shown in place in the knee, the concentric drill is not shown.
Figure 3B:
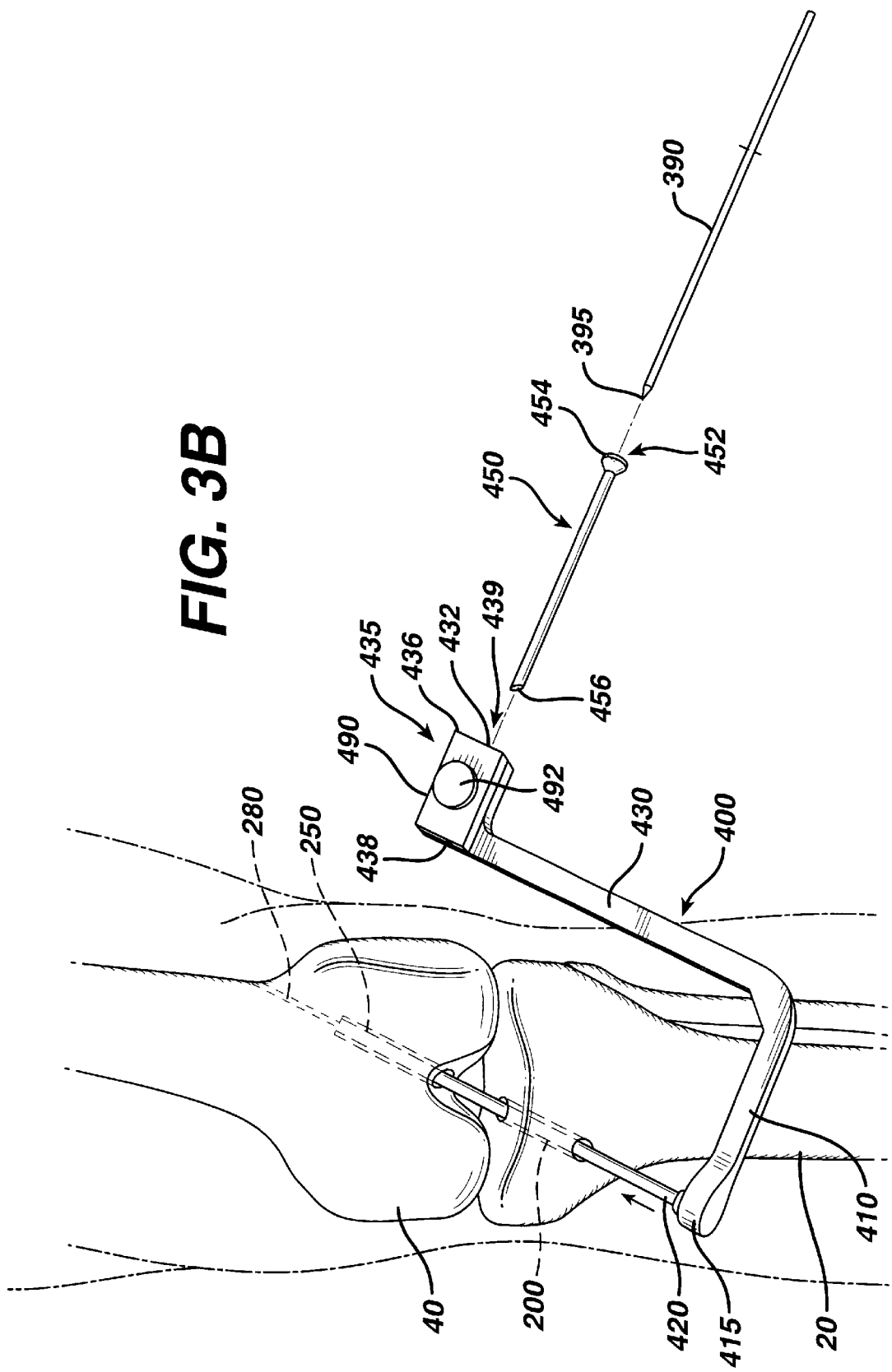
FIG. 3B illustrates the knee joint of FIG. 3A after the tibial and femoral bone tunnels have been drilled out, and illustrates a drill guide being mounted to the knee; also illustrated is a cannula and a trocar drill used for drilling a transverse glue tunnel.
Figure 3C:
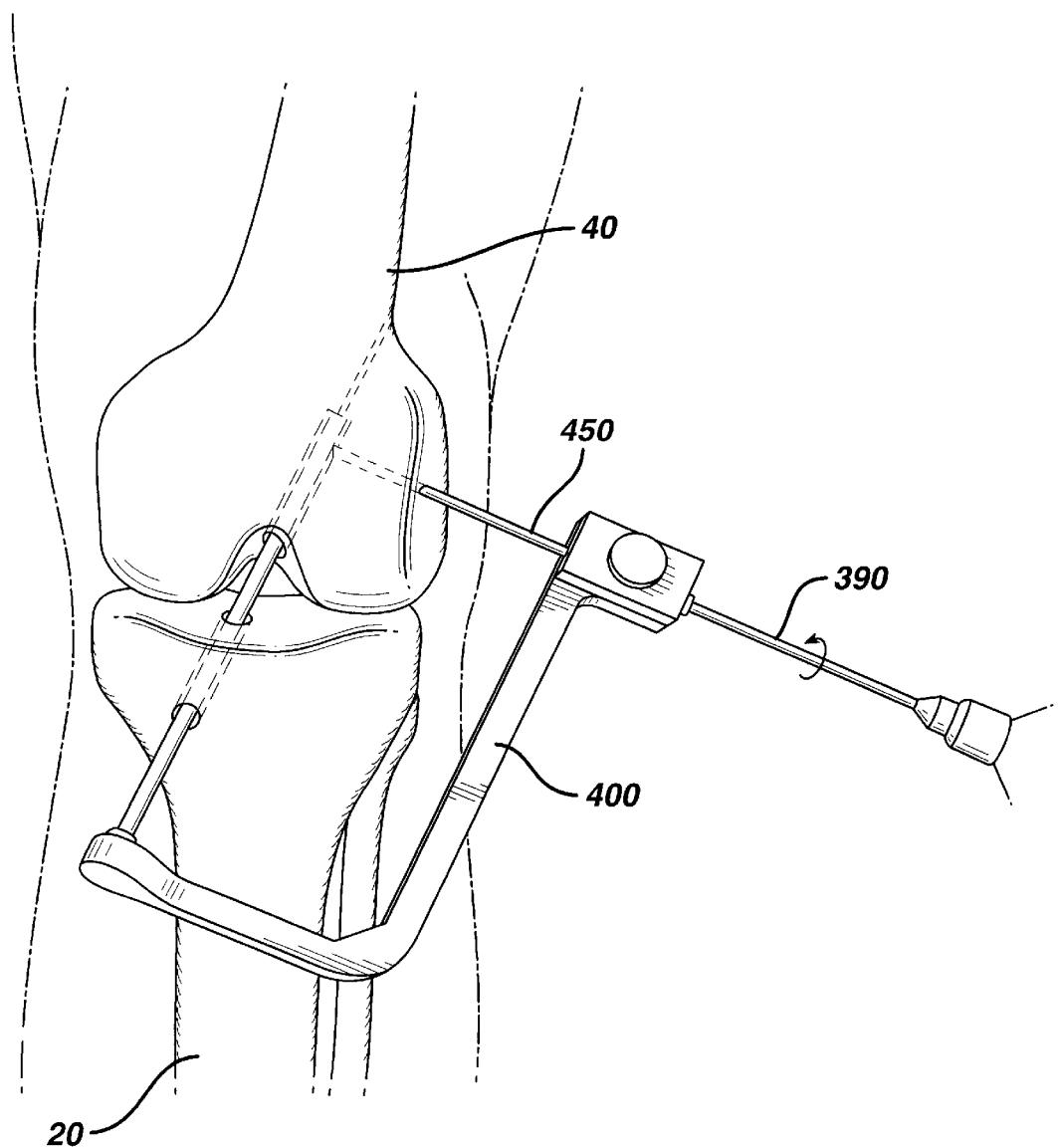
FIG. 3C illustrates a transverse glue tunnel being drilled into the femur in communication with the femoral bone tunnel.
Figure 3D:
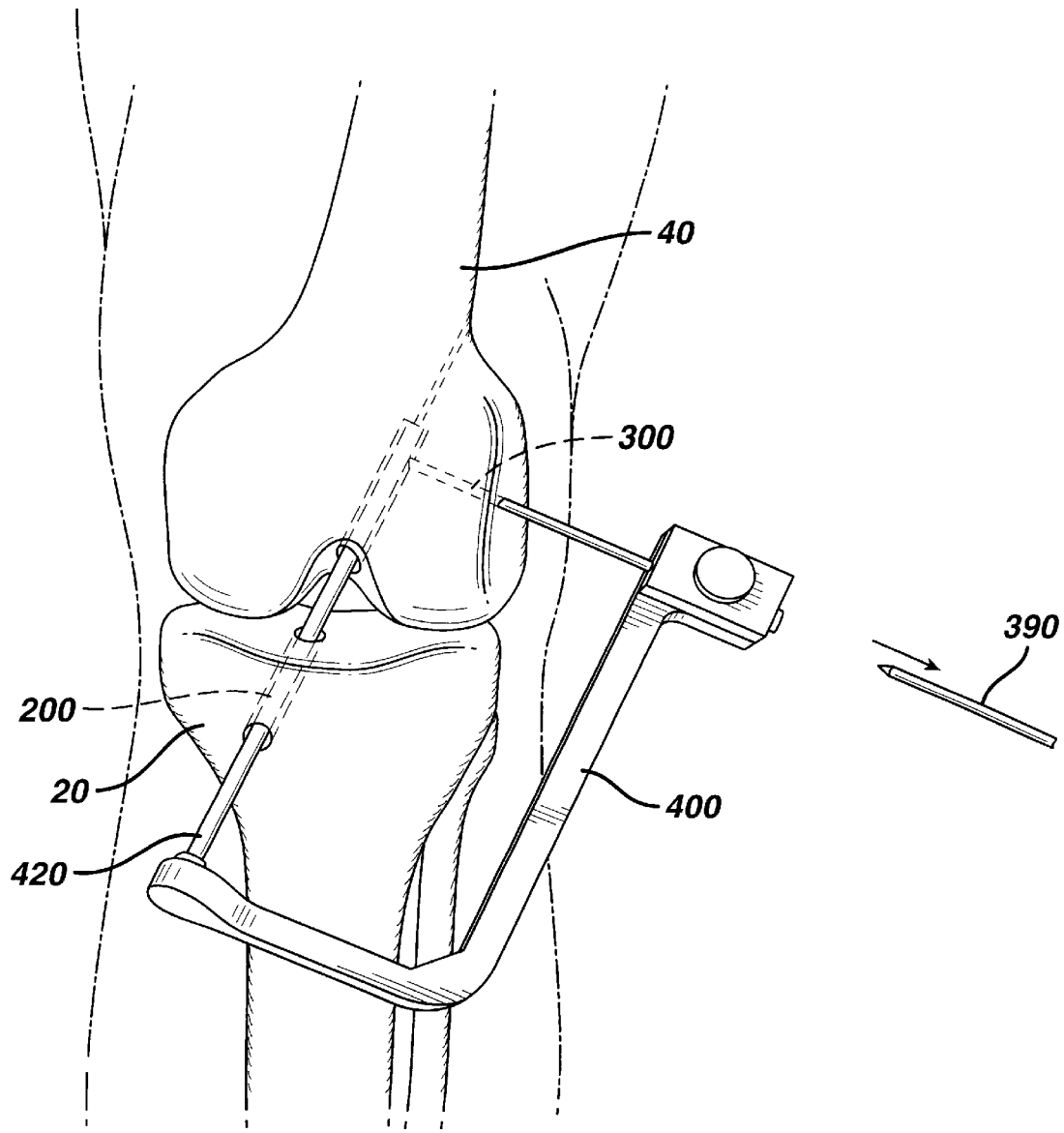
FIG. 3D illustrates the knee after the transverse glue tunnel has been drilled and the drill has been removed.
Figure 3E:
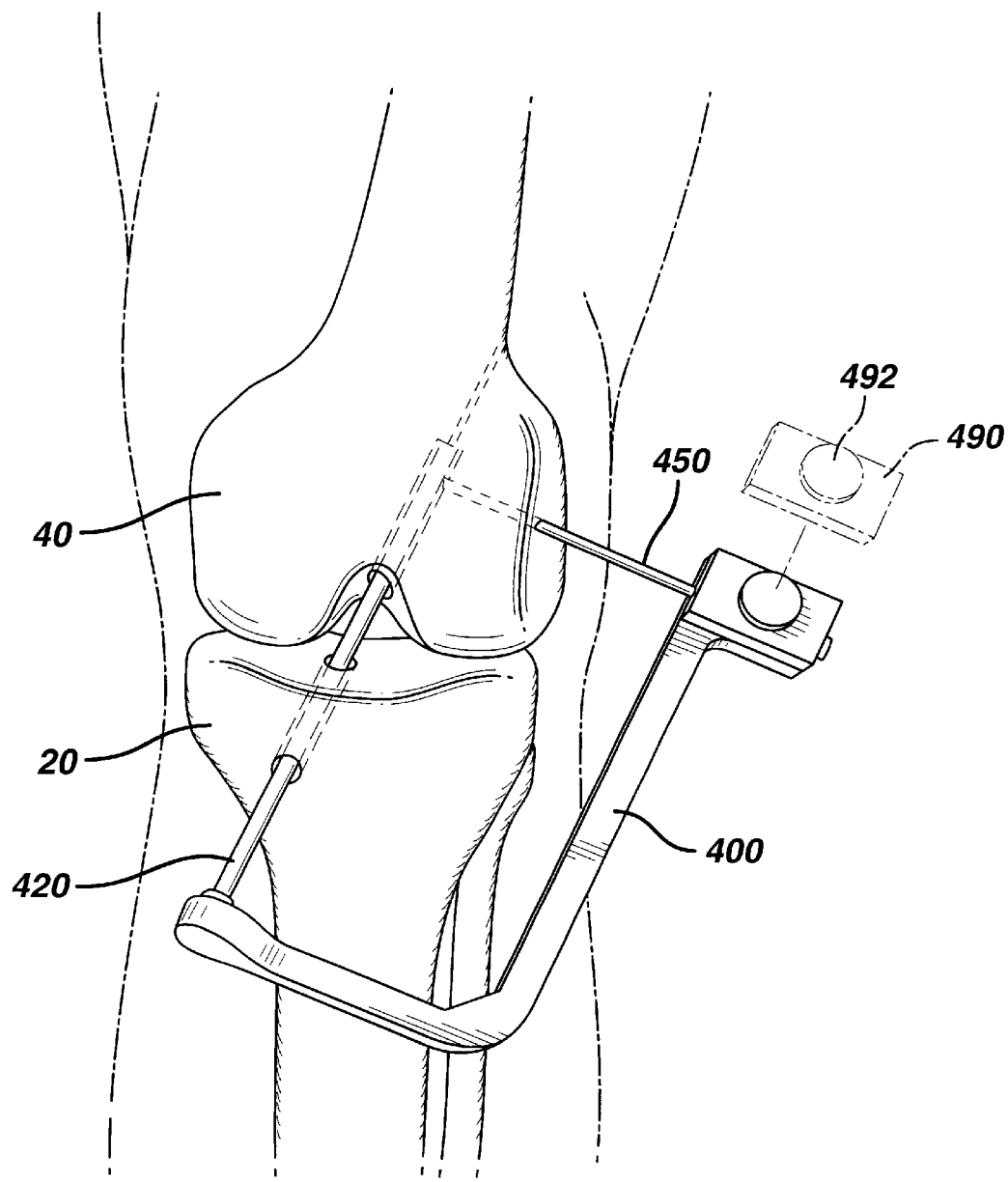
FIG. 3E illustrates a removable clamp on the drill guide which is disengaged prior to removing the drill guide from the knee in order to allow the cannula to remain in place in the glue tunnel.
Figure 4:
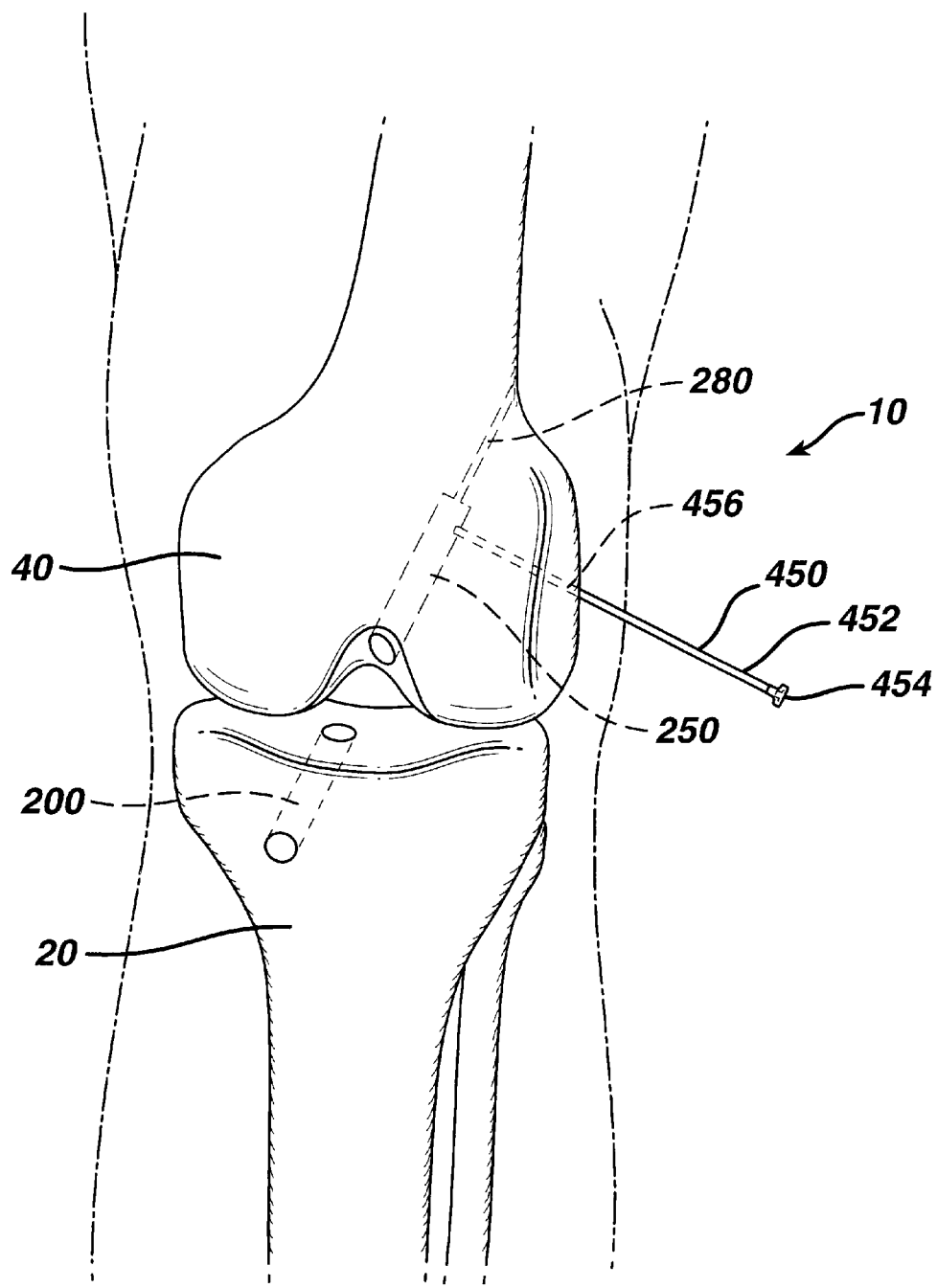
FIG. 4 illustrates the knee with the drill guide removed, and also illustrates a trocar cannula inserted into the glue tunnel; the distal tip of the cannula extends into the femoral bone tunnel.
Figure 5:
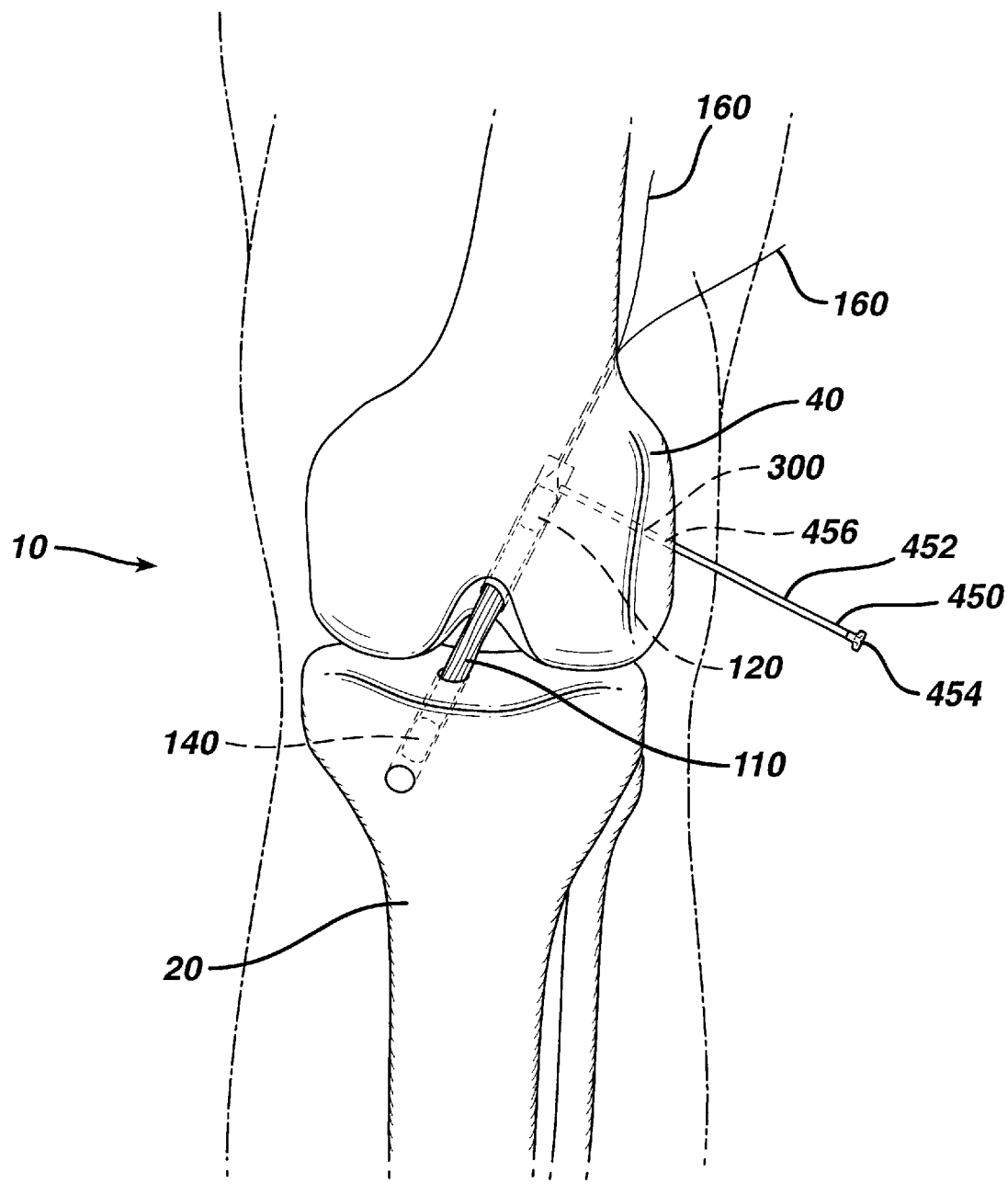
FIG. 5 illustrates the graft being emplaced in the femoral and tibial tunnels by pulling on the suture attached to the femoral bone plug.

After the bone-tendon-bone graft 100 has been harvested, as seen in FIG. 2, it is maintained in a moist condition prior to implantation in a conventional manner. Next, the patient's knee is prepared to receive the graft 100 by drilling tunnels into the femur and tibia as seen in FIGS. 3A. A substantially longitudinal bone tunnel 200 is drilled into the tibia 20 in a conventional manner using conventional surgical equipment. The bone tunnel 200 is seen to have longitudinal passage 205 and longitudinal axis 206. Bone tunnel 200 is additionally seen to have first opening 210 and second opening 220, both openings which are in communication with passage 205. In addition, tibial bone tunnel 200 is seen to have interior surface 225. The femoral bone tunnel 250 is also drilled into the femur using conventional surgical equipment and techniques. The femoral tunnel 250 is seen to have opening 260, longitudinal passage 255 and longitudinal axis 256. The femoral bone tunnel 250 is also seen to have distal end 270 and inner surface 265. Longitudinal axis 256 is seen to be in substantial alignment with longitudinal axis 206. Next, the suture tunnel 280 is drilled into the femur such that the suture tunnel 280 is substantially in longitudinal alignment with the longitudinal axis 256 of the femoral bore hole 250. Suture tunnel 280 is seen to have interior passage 286. In addition, tunnel 280 is seen to have first opening 282 and second opening 284 such that the inner passage of tunnel 280 is in communication with the inner passage 255 of femoral bore hole 250 through opening 282 and also in communication with the exterior of the femur 40 through opening 284. The glue tunnel 300 is seen to be substantially transverse to longitudinal axis 256 of femoral tunnel 250 in a preferred embodiment, but may, if desired, be angulated. Glue tunnel 300 is seen to have interior passage 305 in communication with passage 255 through first opening 307, and in communication with the exterior of femur 40 through second opening 308.

The tunnels 200, 250, and 280 are drilled in a conventional manner using conventional surgical orthopedic drilling equipment. Initially, the surgeon aligns the tibia and femur into the desired position for the procedure. Next, the distal end 355 of pilot pin drill 350 is placed against the outer surface of the tibia and a pilot bone hole is drilled through the tibia and femur by rotating drill 350 with a conventional surgical drill apparatus, until the end 355 exits the femur from opening 284 thus creating tunnel 280, and the pilot bone hole precursors for tunnels 200 and 250. Tunnels 200 and 250 are further formed by drilling with a conventional concentric surgical drill 370 (not shown) having drilling end 375 and inner passage 372, which is mounted over pilot pin drill 350 in a conventional manner. After the drilling of tunnels 200, 250 and 280 has been successfully completed, the pilot pin drill 350 and concentric drill 370 are withdrawn from the tunnels.

Next, the transverse glue tunnel 300 is drilled into the femur. Specifically, as seen in FIGS. 3B–E, the conventional L-shaped drill guide 400 is used to locate and align the transverse tunnel 300. Drill guide 400 is seen to have first and second legs 410 and 430. At the end 412 of leg 410 is located the base receiver 415. Extending up from base receiver 415 is the locating leg 420 having proximal end 422, and distal end 424. If desired, although optional, drills and other instruments can be inserted through base receiver 415 into and through locating leg 420 by providing appropriate openings and passageways. Leg 430 is seen to have end 432 and drill receiver 435 mounted thereto, having first opening 436, second opening 437 and internal passageway 439 in communication with both openings. Locating leg 420 is seen to be mounted in tibial bone hole 200.

Then, cannula 450 having drill 390 with distal drilling end 395 located therein, is inserted into and through opening 432 of drill guide 400, and the drill 390 is rotated by a conventional surgical drill to drill out glue tunnel 300 and place cannula 450 in tunnel 280. Cannula 450 is seen to have internal passage 452, proximal end opening 454 in communication with passage 452 and distal end opening 456 in communication with passage 452. After the tunnel 300 is completely formed, drill 390 is removed and guide 400 is removed by removing retention bracket 490 secured by screw 492 and pulling out leg 420 from passage 200, leaving cannula 450 in glue tunnel 280. Although not preferred, the method of the present invention can be performed without the use of cannula 450. Also, if desired, cannula 450 may be placed into the tunnel 280 subsequent to drilling.

Referring now to FIGS. 4–9, after the bone tunnels 200 and 250, the suture tunnel 280, and glue tunnel 300 have been drilled, the longitudinal axes 206 and 256, respectively, of the bone tunnel 200 and bone tunnel 250 are placed in alignment by the surgeon. Next, the conventional suture 160 mounted to the femoral bone plug 120 is threaded through the interior passages of 205 and 255 of the tibial tunnel 200 and the femoral tunnel 250, respectively, and is further threaded through and out of the suture tunnel 280. Next, the surgeon pulls the suture 160 such that the femoral plug passes into passage 255 of the femoral tunnel 250 and the tibia plug passes into passage 205 of the tibia tunnel 200.

Figure 6:
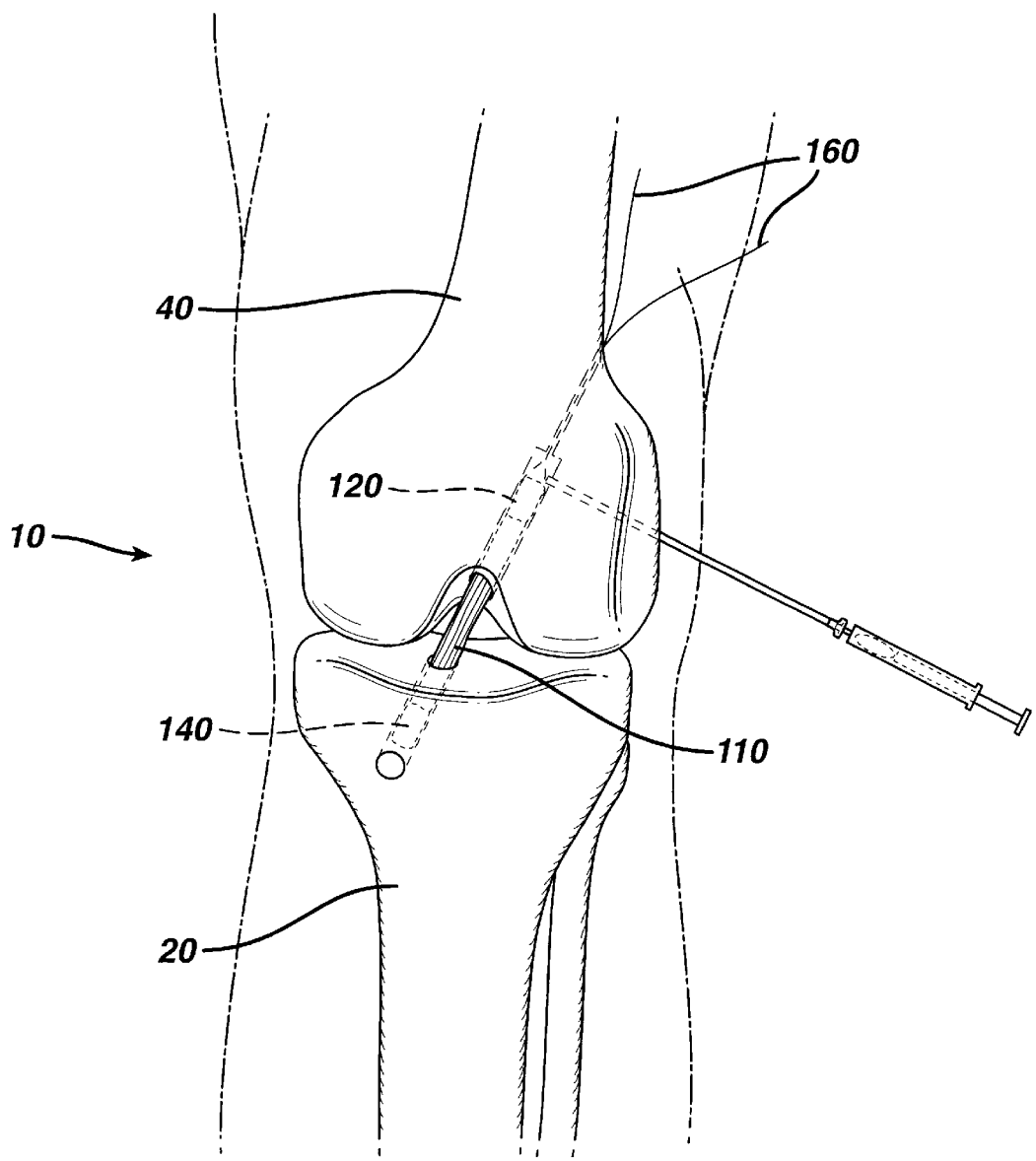
FIG. 6 illustrates the tibial and femoral bone plugs in place in the bone tunnel; and, bone glue being introduced into the cannula in the femoral bone tunnel through the transverse glue hole to secure the femoral bone plug by using a hypodermic needle to inject the glue into the cannula.
Figure 7:
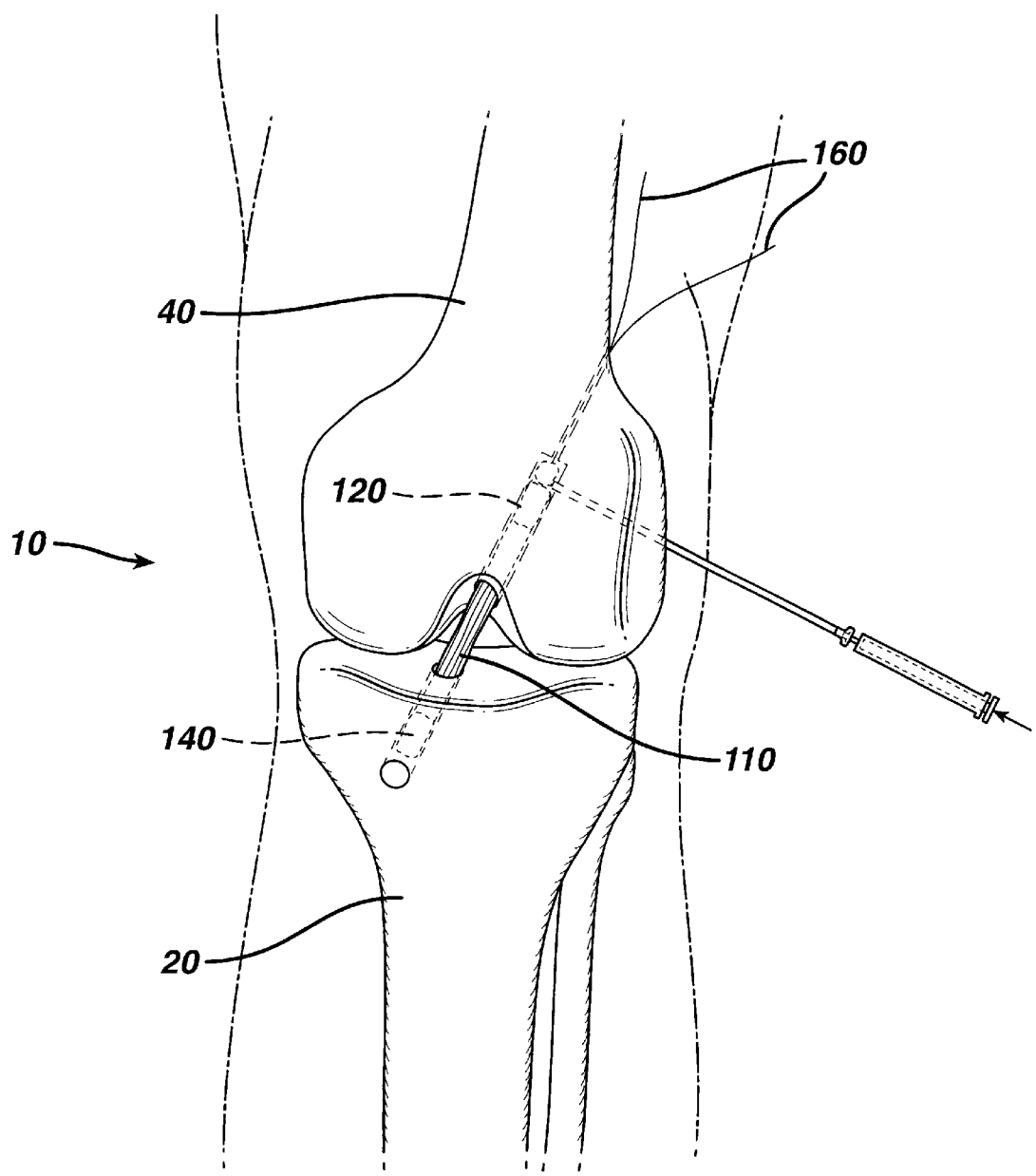
FIG. 7 illustrates a bolus of glue in the femoral tunnel between the top of the femoral plug and the distal end of the femoral tunnel injected via the needle of the syringe placed in the cannula.
Figure 8:
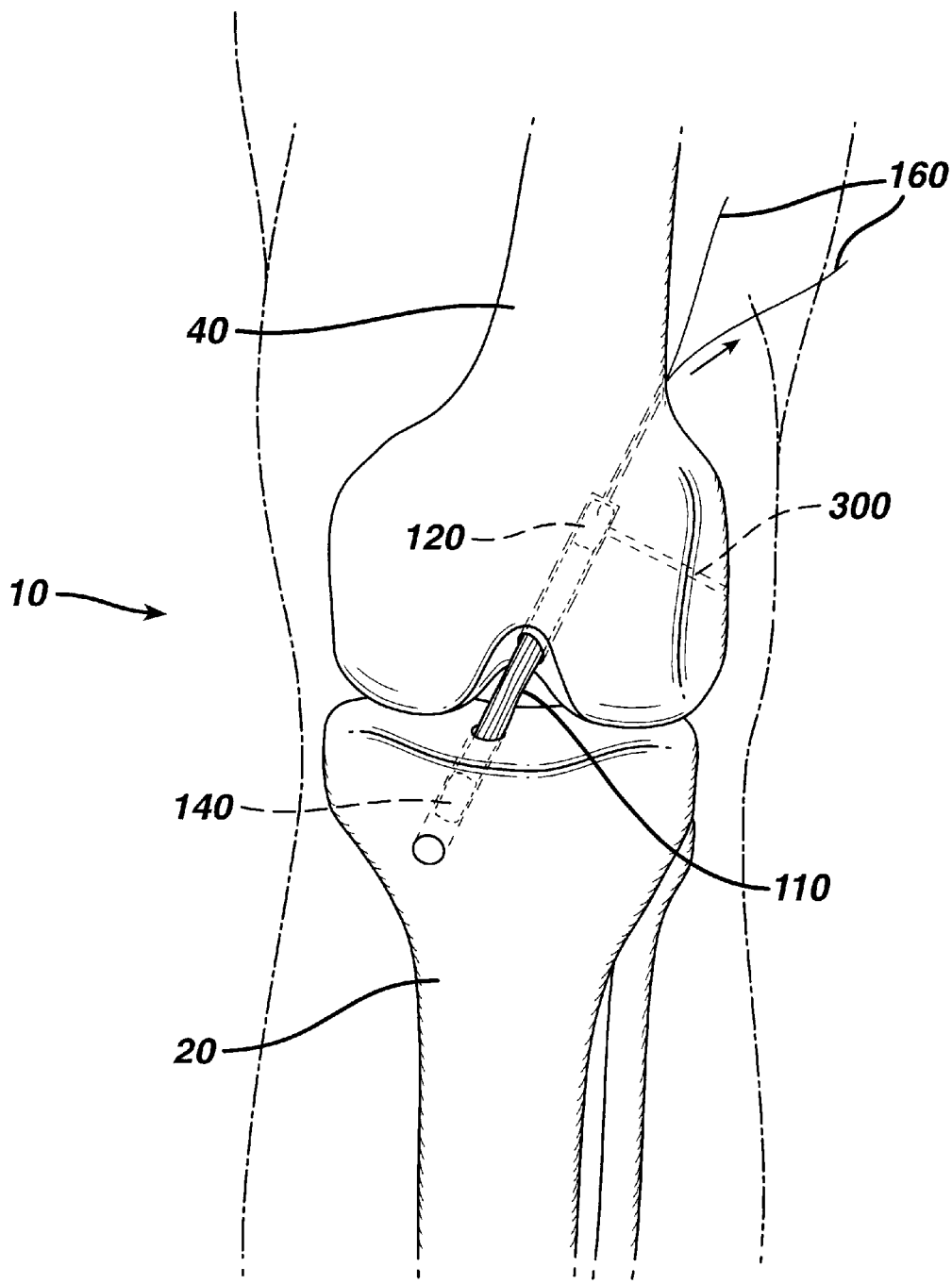
FIG. 8 illustrates a bolus of glue on top of the femoral plug in the femoral bone tunnel prior to setting the femoral plug in place; the cannula has been removed.
Figure 9:
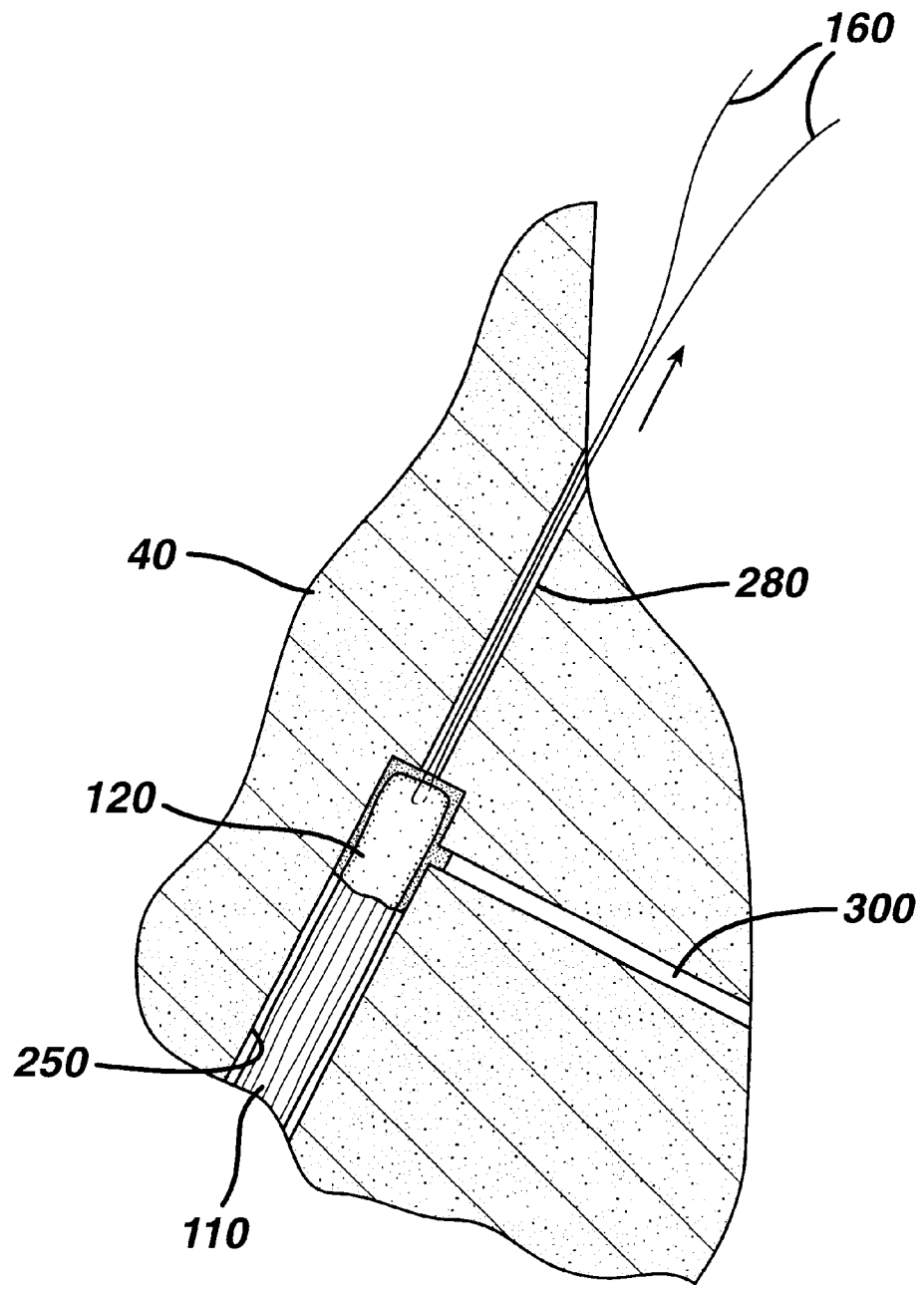
FIG. 9 is a partial cross-sectional view illustrating the graft after the femoral plug has been pulled into place, and the glue has been spread about the femoral plug and femoral tunnel.

The surgeon is careful to locate the distal end 135 of the femoral bone plug 120 immediately below the opening 307. At this time, the tibial bone plug 150 is either partially or completely located in bone tunnel 200. Next, the surgeon injects a bone glue or bone cement into the cannula 450 using a conventional syringe 500 such that a bolus of the bone cement or bone glue 550 flows through the interior passage of cannula 450, through the interior of glue tunnel 300, and finally into the interior of bone tunnel 250 as seen in FIGS. 6, 7 and 8. Syringe 500 is seen to have barrel 510 for receiving glue 550 plunger 520 and hollow needle 530. The surgeon then removes the trocar 450 and syringe 500 from the glue tunnel 300, next the surgeon pulls on the ends of suture 160 thereby pulling the bone plug 120 into position in the femoral bone tunnel 250 such that the distal end 135 or the bone plug 125 abuts the distal end 270 of the bone tunnel 250. At the same time the glue 550 is spread in and about the inner surface 265 of the bone tunnel 250 and the outer surface 125 of the plug 120 thereby securing the bone plug in place upon the curing of bone glue or bone cement 550. The suture 160 may then be removed from the femoral bone plug 120, or the ends external to the femur may be cut. The tibial bone plug 140 can then be secured in the bone tunnel 200 in a conventional manner using, for example, bone screws or pins. Or, if desired, an additional transverse glue hole can also be drilled into the tibia in communication with tibial tunnel 200, and bone glue or bone cement 550 may be similarly delivered by the surgeon into the bone tunnel 200 through the tibial glue tunnel. Although not preferred, the surgeon may inject a bolus of bone glue 550 into femoral bone tunnel 250 prior to locating the femoral bone plug 120 in tunnel 250.

Figure 10:
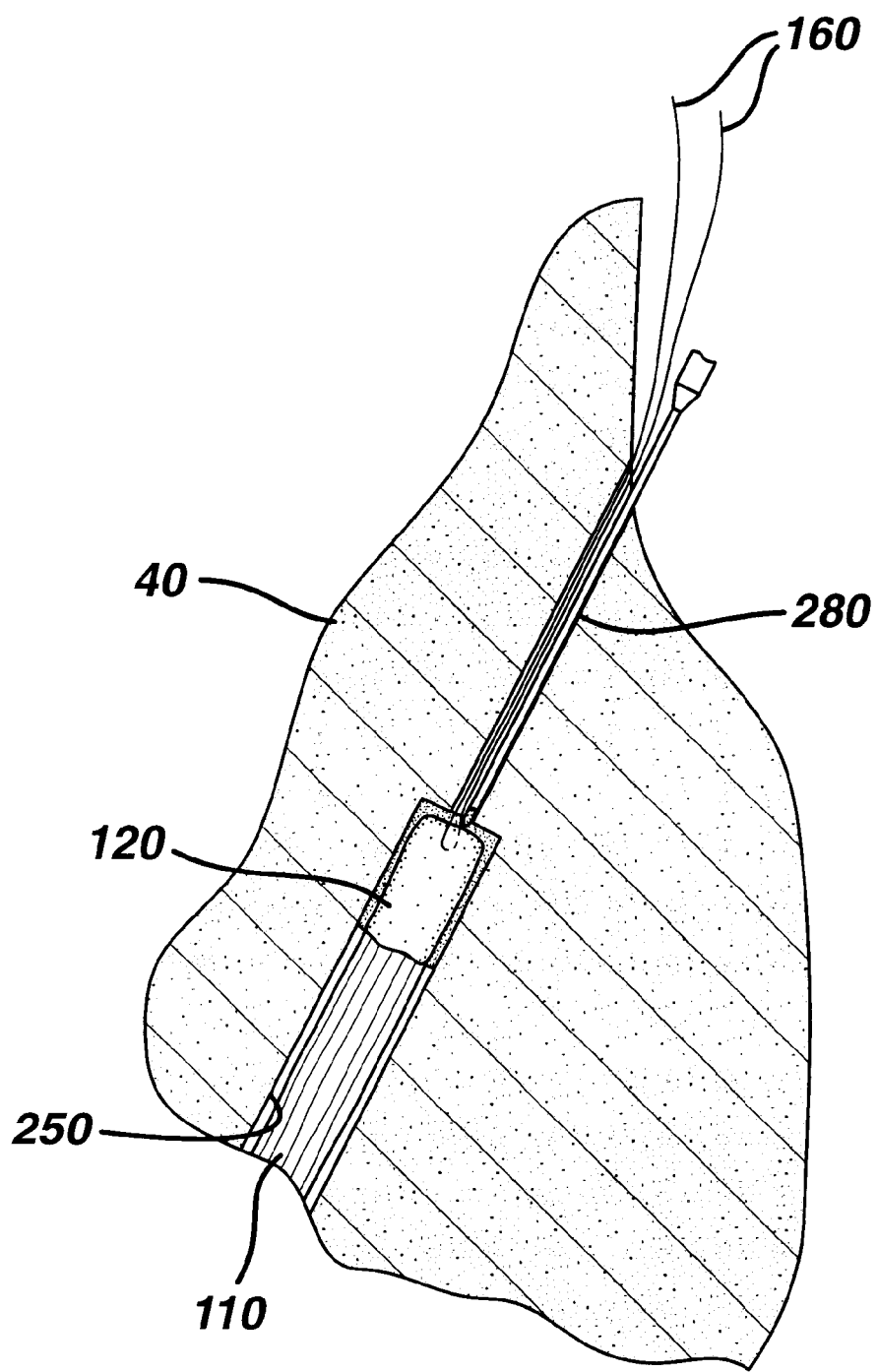
FIG. 10 illustrates an alternate embodiment of the present invention, wherein the adhesive is introduced into the femoral bone tunnel through the distal suture hole in the femur in communication with the femoral bone tunnel, to secure the femoral bone plug.

FIG. 10 illustrates and alternate embodiment of an ACL reconstruction method of the present invention. As seen in FIG. 10, the method steps are similar to that of the previously described preferred method, except that the glue tunnel 300 is not drilled and utilized. Instead, the glue 550 is injected via syringe 500 through the suture tunnel 280 into the femoral bone tunnel 250 when the bone plug 120 is partially engaged in the bone tunnel 250, or prior to inserting the bone plug 120 into femoral bone tunnel 250.

Figure 11A:
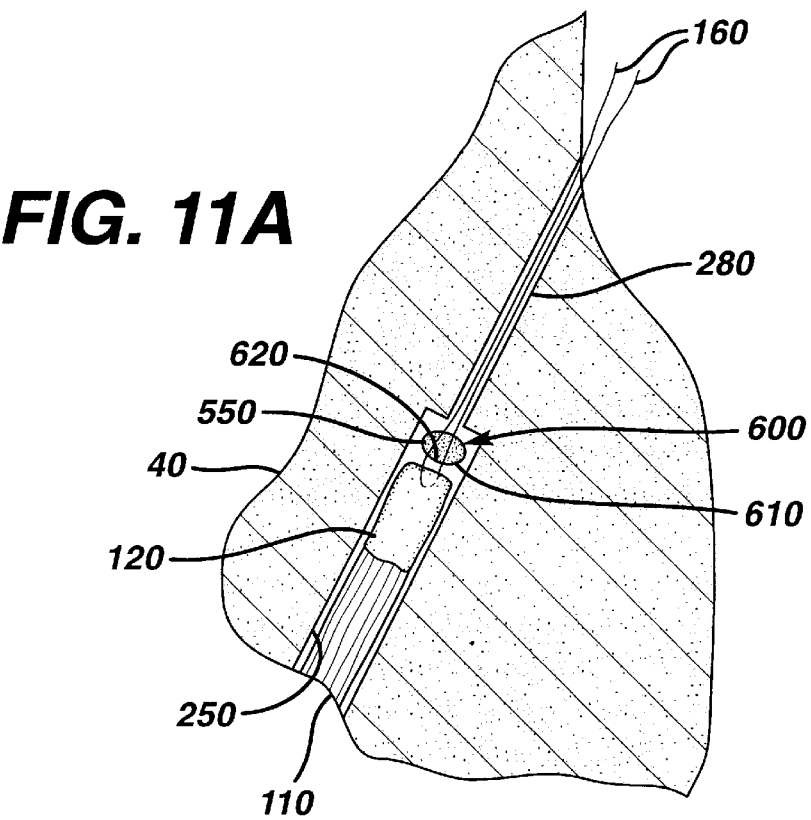
FIGS. 11A–B illustrate another embodiment of the present invention wherein the bone glue is contained in a frangible capsule which is introduced in the femoral bone hole prior to emplacing the femoral bone plug, and the capsule is crushed when the femoral plug is pulled into place, thereby allowing the glue to exit the capsule and make contact with the bone plug and the interior surface of the femoral bone tunnel.
Figure 11B:
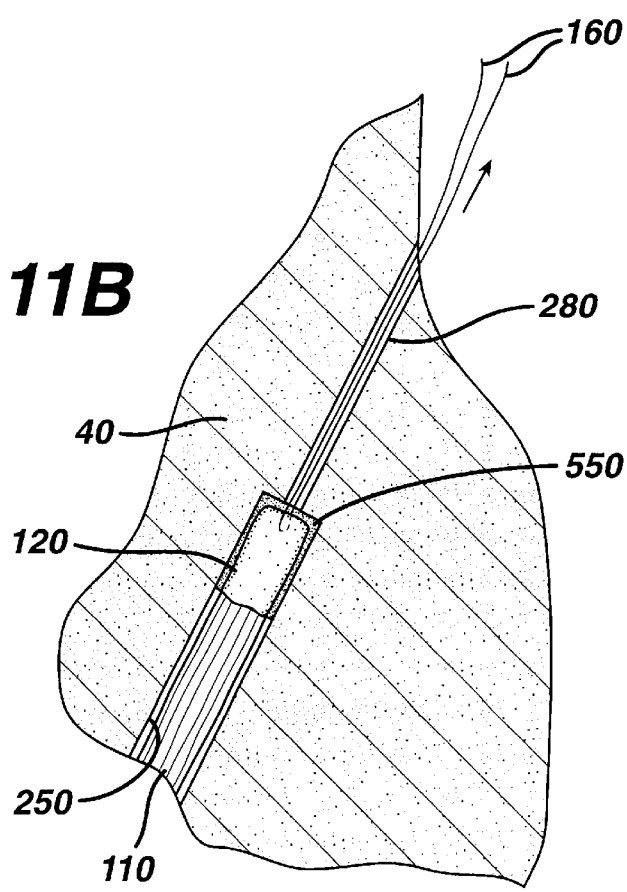

Yet another embodiment of the ACL reconstruction method of the present invention is illustrated in FIGS. 11A–B. In FIGS. 11A–B, the method steps are similar to that of the method steps of the preferred embodiment of the present invention. However, rather than drilling a transverse bone tunnel or injecting bone glue or cement through the suture tunnel, a frangible capsule 600 containing bone glue or bone cement 550 is inserted into the femoral tunnel 250 prior to introducing the plug 120 into the tunnel 250. Then the surgeon pulls the suture threads 60 upwardly such that the distal end of the bone plug engages the frangible capsule 600 thereby breaking open the shell 610 of capsule 600 and causing glue 550 contained in the interior 620 of capsule 600 to be spread about the inner surface 265 of the bone tunnel 250 and the outer surface 125 of the plug 120.

The methods of the present invention preferably will utilize bone plugs and tendons and ligaments harvested from autologous tissue in the patient's knee or other areas of the body as illustrated in FIGS. 1 and 2 using conventional surgical techniques. However, if desired, artificial bone plugs and tendons may be utilized. The bone plugs may consist of conventional bone substitute materials including polylactic acid and polyglycolic acid as well as bioceramics such as tricalcium phosphate, calcium phosphate, tetracalcium phosphate and hydroxyapatite, and any copolymers, mixtures or blends thereof, and the like and equivalents thereof. The artificial tendons or ligaments can consist of conventional tendon replacement materials including carbon fibers, polyethylene terephthalate, polytetrafluoroethylene (PTFE), polypropylene, as well as biodegradable polymers including polylactic acid, polyglycolic acid, polydioxanone, polycarbonate, polycaprolactone, and copolymers thereof, and the like, and combinations thereof and equivalents thereof.

The amount of glue or cement used to secure the bone plugs in the bone tunnels in the method of the present invention will be sufficient to effectively maintain the bone plugs in place after curing and setting. The amount that is used will depend upon several factors including the characteristics and nature of the bone plug, the nature and characteristics of the bone cement or glue, the size and length of the bone tunnels, the nature and characteristics of the bone glue or cement and the individual characteristics of the patient.

The term "adhesive" is used collectively herein to include bone glues and bone cements. The bone glues which can be used in the practice of the present invention include conventional biocompatible bone glues including 2-octyl cyanoacrylate and the like and equivalent thereof. The bone cements which can be used in the practice of the present invention include conventional biocompatible bone cements such as polymethylmethacrylate and the like. The bone glues and bone cements may be absorbable or nonabsorbable.

The frangible capsules 600 useful in the practice of the embodiment of the method of the present invention will typically have a hollow body having a shell 610 and interior 620. The interior 620 of the shell 610 will be filled with bone cement or bone glue 550. The shell will typically be made out of biocompatible material which is frangible and will break or rupture when squeezed or compressed. Examples of such shell materials include gelatin, and conventional bioabsorbable and bioresorbable polymeric materials, and the like.

The following example is representative of the principles and practice of the present invention although not limited thereto.

EXAMPLE

A patient was anesthetized in accordance with conventional anesthesiology procedures. The patient's knee joint was prepared for an ACL reconstruction in a conventional manner. Incisions were made into the knee exposing the lower part of the femur, the upper part of the tibia, the tibial tendon and the patellar tendon. A bone-plug-tendon-bone-plug bone graft was harvested from the patellar bone, the tibial tendon and the tibia. Then, a conventional pilot pin wire drill was utilized to drill a bone tunnel through the tibia into and out of the femur thereby creating the suture tunnel and precursor tibial and femoral bone tunnels. Next, a conventional concentric drill was placed over the drill/guide wire and the drill was operated in a conventional manner to create the tibial tunnel and the femoral bone tunnel. The drills were then removed. Then, a conventional drill guide was mounted on the patient's tibia and femur. Next, a transverse glue tunnel was drilled into the femur utilizing the drill guide and a conventional trocar drill and cannula, the tunnel intersecting the femoral bone tunnel such that the interior passage of the femoral bone tunnel was in communication with the transverse glue tunnel. After removing the drill, the cannula was left in place in the glue tunnel. Next, the surgeon prepared the bone tendon, bone graft by drilling a transverse hole through the femoral plug and inserting a length of conventional Ethibond® surgical suture therethrough. Next, the surgical suture was threaded through the tibial tunnel, the femoral tunnel and through and out of the suture tunnel so that both ends of the suture were exterior to the femur. Next, the surgeon proceeded to pull the bone-tendon-bone graft through the tibial tunnel and further into the femoral tunnel such that the distal end face of the femoral bone plug was located just proximal to the opening into the glue tunnel. Next, the surgeon mounted a the needle of conventional syringe containing about 40 cc of 2-octyl cyanoacrylate bone glue into the trocar cannula, and a bolus of the bone cement was injected through the cannula into the femoral bone tunnel, and the cannula was removed. Next, the surgeon continued to pull on the ends of the suture such that the distal face of the bone plug was in contact with the distal end of the femoral tunnel, effectively spreading the bolus of bone glue about the interior surfaces of the femoral bone tunnel and also over the exterior surfaces of the femoral bone plug such that the bone plug was effectively bonded to the interior surfaces of the bone tunnel by the bone glue. After waiting a sufficient period of time for the bone glue to cure, the surgeon cut off the ends of the suture, and the incisions were then approximated in a conventional manner utilizing conventional surgical sutures. Next, the surgeon secured the tibial plug to the tibial bone hole in a conventional manner utilizing a conventional bone screw. The patient's knee was then immobilized, and the ACL reconstruction was completed.

The advantages of the improved ACL reconstruction methods of the present invention are numerous. It is now possible to perform an ACL reconstruction without having to use mechanical fasteners to maintain a femoral bone plug in place. In addition, the length of the surgical procedure can be reduced since it not necessary to drill additional bone tunnels to receive mechanical fasteners such as screws and pins.

Although this invention has been shown and described with respect to detailed embodiments thereof, it will be understood by those skilled in the art that various changes in form and detail may be made without departing from the spirit and scope of the claimed invention.

We claim:

1. A method of performing a surgical reconstruction of an anterior cruciate ligament, comprising:
   providing a bone-tendon graft comprising at least one bone plug connected to a section of tendon, the bone plug having an outer surface;
   drilling a first substantially longitudinal bone tunnel into a patient's tibia;
   drilling a second substantially longitudinal bone tunnel into a femur, and said second bone tunnel having an inner surface;
   inserting the bone plug into the femoral tunnel; and,
   introducing an adhesive into the femoral tunnel,
   wherein the adhesive is in at least partial contact with the outer surface of the bone plug and the inner surface of the femoral bone tunnel.

2. The method of claim 1 wherein the bone tendon graft comprises a section of patellar tendon having a proximal end and a distal end, a patellar bone plug attached to the distal end of the tendon and a tibial bone plug attached to the proximal end of the tendon.

3. The method of claim 1 wherein the adhesive is a bone glue.

4. The method of claim 1 wherein the adhesive is a bone cement.

5. The method of claim 3 wherein the glue is bioabsorbable.

6. The method of claim 4 wherein the cement is bioabsorbable.

7. The method of claim 2 additionally comprising the step of fixating the tibial bone plug in the tibial tunnel.

8. The method of claim 4 wherein the cement comprises polymethylmethacrylate.

9. The method of claim 3 wherein the glue comprises 2-octyl cyanoacrylate.

10. The method of claim 1, wherein a transverse bone tunnel is drilled into the femur substantially transverse to the femoral tunnel, wherein the transverse tunnel is in communication with the femoral tunnel.

11. The method of claim 10 wherein the adhesive is introduced by injecting through the transverse tunnel into the femoral tunnel.

12. The method of claim 1, wherein the femoral tunnel is a blind bore hole, having a distal bottom.

13. The method of claim 12, wherein a suture tunnel substantially in alignment with the femoral tunnel is drilled through the distal bottom and out through the femoral bone such that the suture tunnel is in communication with the femoral tunnel.

14. The method of claim 13, wherein the adhesive is introduced into the femoral tunnel through the suture tunnel.

15. The method of claim 13, wherein the bone plug has a suture mounted thereto.

16. The method of claim 15, wherein the adhesive comprises a frangible capsule having an interior volume containing adhesive that is placed into the femoral bore hole prior to inserting the bone plug.

17. The method of claim 1 wherein the adhesive is introduced into the femoral tunnel prior to inserting the femoral bone plug.

18. The method of claim 1 wherein the bone plug comprises autologous bone.

19. The method of claim 1 wherein the bone plug comprises an artificial bone substitute material.

20. The method of claim 1 wherein the tendon comprises an artificial tendon substitute material.

21. A method of fixating a bone plug in a bone tunnel, comprising:

providing a bone plug the bone plug having an outer surface;

drilling bone, said bone tunnel having an inner surface;

inserting the bone plug into the bone tunnel; and, introducing an adhesive into the bone tunnel, wherein the adhesive is in at least partial contact with the outer surface of the bone plug and the inner surface of the bone tunnel.

* * * * *